United States Patent
Bondarowicz et al.

(10) Patent No.: US 6,513,368 B2
(45) Date of Patent: Feb. 4, 2003

(54) METHOD OF MONITORING ENGINE LUBRICANT CONDITION

(75) Inventors: Frank Bondarowicz, Park Ridge, IL (US); Kevin R Calstrom, Ft. Wayne, IN (US); Gerald L Larson, Ft. Wayne, IN (US)

(73) Assignee: International Truck Intellectual Property Company, L.L.C., Warrenville, IL (US)

( * ) Notice: Subject to any disclaimer, the term of this patent is extended or adjusted under 35 U.S.C. 154(b) by 0 days.

(21) Appl. No.: 10/184,721

(22) Filed: Jun. 28, 2002

(65) Prior Publication Data

US 2002/0166366 A1 Nov. 14, 2002

Related U.S. Application Data

(62) Division of application No. 09/791,434, filed on Feb. 22, 2001.

(51) Int. Cl.[7] .......................... G01N 33/26; G01M 17/00
(52) U.S. Cl. ......................................... 73/53.05; 701/30
(58) Field of Search .............................. 73/53.05, 61.76, 73/32 R; 123/376, 463, 452; 324/672, 663; 508/545, 294; 701/30

(56) References Cited

U.S. PATENT DOCUMENTS

| | | | | |
|---|---|---|---|---|
| 2,234,096 A | * | 3/1941 | Teter et al. .................. | 508/545 |
| 2,287,713 A | * | 6/1942 | Udale .......................... | 123/376 |
| 2,378,036 A | * | 6/1945 | Reggio ........................ | 123/463 |
| 2,493,587 A | * | 1/1950 | Lee ............................. | 123/452 |
| 4,281,533 A | * | 8/1981 | Eesley et al. ............... | 73/61.76 |
| 4,306,525 A | * | 12/1981 | Faxvog ..................... | 123/196 S |
| 4,506,337 A | * | 3/1985 | Yasuhara ..................... | 701/30 |
| 4,966,032 A | * | 10/1990 | Takeuchi ................... | 73/53.05 |
| 5,262,732 A | * | 11/1993 | Dickert et al. .............. | 324/672 |
| 5,604,441 A | * | 2/1997 | Freese et al. ............... | 324/663 |
| 5,798,452 A | * | 8/1998 | Martin et al. ............... | 73/32 R |
| 6,004,910 A | * | 12/1999 | Bloch et al. ................ | 508/294 |

* cited by examiner

Primary Examiner—Hezron Williams
Assistant Examiner—J L Politzer
(74) Attorney, Agent, or Firm—Jeffrey P. Calfa; Neil T. Powell; Dennis Kelly Sullivan

(57) ABSTRACT

A method for generating indicators relating to the condition of lubricating oil in an internal combustion engine. A set of variables relating to operation of the internal combustion engine serve as proxy variables for brake mean effective pressure developed by the internal combustion engine. Operation of an engine is monitored to develop values for the proxy variables. Soot being added to the lubricating oil from the developed values and accumulated to provide an estimate of total soot in the lubricating oil. Lubricating oil temperature is periodically monitored and a history of the lubricating oil temperature measurements is kept to allow generation therefrom of an estimate of shear of the lubricating oil. Accumulated estimate of soot is kept as a distance remaining until the lubricating oil becomes unsuitable for continued use in the internal combustion engine. Similarly, estimated shear is expressed as a distance until the lubricating oil is to be replaced. Additional factors may be monitored and similarly used to determine the distance until an oil change is required, including the dielectric coefficient of the lubricating oil, temperature history of the oil and total cylinder firing events.

4 Claims, 9 Drawing Sheets

METHOD OF MONITORING ENGINE LUBRICANT CONDITION

This is a divisional application claiming priority of application Ser. No. 09/791,434, filed Feb. 22, 2001.

BACKGROUND OF THE INVENTION

1. Field of the Invention

The present invention relates generally to a method for determining the condition of motor oil, and more particularly to a method of monitoring motor oil during diesel engine operation in implementing an economically efficient oil change regimen.

2. Description of the Prior Art

Truck fleet operation is a highly competitive and fleet operators are highly conscious of balancing preventive maintenance costs and fleet operational readiness with repair and replacement costs. While cost effective fleet management and readiness requirements demand the practice of preventive maintenance, some of these practices are based, for lack of individual vehicle information, on potentially overly conservative regimens derived from broad statistical studies. An example of such a practice is manufacturers' recommendations relating to changes of motor oil. A change of motor oil costs money and removes a vehicle from service. While frequent changes of motor oil doubtless extend the service life of a vehicle and are, up to a point, economically advisable, they can become wasteful and uneconomic if excessively frequent.

Changes of motor oil are necessitated by the fact that motor oil loses its lubricating properties with use. With loss of adequate lubrication an engine is exposed to wear and damage. The degree, and character, of motor oil degradation is related to a number of factors, including temperature cycling of the lubricant which relates to oxidation of the oil, and the possibility of the addition of foreign material to the oil (e.g. soot). Manufacturers' recommended oil change schedules are typically based on a conservatively short estimate of the useful life of the oil.

U.S. Pat. No. 5,987,976 reports the practice of modifying estimates of engine oil useful life by taking into account the conditions under which an engine operates. The '976 patent asserts that a short coming of such a method is that it does not indicate the condition of the motor oil at any given moment. Put another way, the method is a refinement of statistical methodology and is handicapped by the use of operator impressions of "operating conditions" (e.g. vehicle loads, prevailing air temperature, etc.), and the lack of quantifiable inputs relating to specific trucks.

In diesel engines, engine oil condition is primarily related to soot accumulation and molecular degradation due to shear and exposure to high temperatures. Soot is a by-product of incomplete combustion of hydro-carbon fuel, which can result from a number of factors, such as use of low volatility diesel fuel blends at low ambient temperatures and operation of an engine at a disadvantageous point on the engine torque curve. In a simplified sense, high engine loads over extended periods of time result in cylinder blow-by which adds soot to the oil and produces localized high temperatures in the oil leading to molecular degradation. Soot moves from the cylinder to the engine oil as a result of cylinder blow-by or by adhesion to the cylinder walls from which it is swept up by the piston rings into the oil. Soot becomes an issue in engine oil when the amount of soot overwhelms dispersants in the oil and begins to agglomerate into particles of sufficient size to damage the engine. Soot intrusion to the engine oil may be estimated as a function of Brake Mean Effective Pressure (BMEP), which serves as a proxy for engine load, and engine revolutions (n). $C_0$ is a proportionality constant.

$$\text{SOOT} = C_0 \int BMEP \, dn \text{ for } n=0 \text{ to } n=M \tag{1}$$

Engine oil molecules are subject to shear due to the mechanical action of tappets, bearings and the oil pump. Shear may also depend upon the type of fuel injector used in the engine. Some fuel injectors employ high pressure engine oil, an additional shear contribution source. For a particular engine design, shear is a function of total revolutions of the engine, not vehicle mileage, since the last oil change. Ko is a proportionality constant.

$$\text{SHEAR} = K_0 \int dn \text{ for } n=0 \text{ to } n=M \tag{2}$$

Other factors are known to contribute to early oil wear, particularly if engine duty cycles are of short duration. Water can contaminate engine oil from air entering through the oil filler nozzle or from the engine cooling system. If an engine does reach or maintain a minimum threshold operating temperature, water which has contaminated the oil will not be forced by evaporation from the oil. While small amounts of water are not harmful, water combines with sulfur compound combustion by-products to form highly corrosive acids in the engine oil, particularly $H_2SO_4$. $H_2SO_4$ can overwhelm basic additives to the engine oil and damage an engine. While it is technically inappropriate to refer to engine oil as having a ph factor, water dispersed in the engine oil has a ph factor. Engine oil additives are designed to give water contaminants in the engine an elevated (i.e. basic) ph to neutralize low levels of $H_2SO_4$ dissolved in the water. Excessive intrusion of $H_2SO_4$ overwhelms the additives.

Another possible engine contaminant is ethylene glycol, which can escape from the engine coolant system. Fuel contamination is also a possibility. Both of these contaminants reduce the lubricity of engine oil and may indicate engine damage.

What is needed is a system implementing a model of engine oil deterioration the variables of which can be effectively measured during engine operation. Preferably the variables can be obtained with no, or a minimal number of, additional sensors.

SUMMARY OF THE INVENTION

According to the invention there is provided a method for generating indicators relating to the condition of lubricating oil in an internal combustion engine. A set of variables relating to operation of the internal combustion engine serve as proxy variables for brake mean effective pressure developed by the internal combustion engine. Operation of an engine is monitored to develop values for the proxy variables. Soot being added to the lubricating oil from the developed values and accumulated to provide an estimate of total soot in the lubricating oil. Lubricating oil temperature is periodically monitored and a history of the lubricating oil temperature measurements is kept to allow generation therefrom of an estimate of shear and oxidation of the lubricating oil. Accumulated estimate of soot is kept as a distance remaining until the lubricating oil becomes unsuitable for continued use in the internal combustion engine. Similarly, estimated shear is expressed as a distance until the lubricating oil is to be replaced. Additional factors may be monitored and similary used to determine the distance until an oil change is required, including the dielectric coefficient of the lubricating oil, temperature history of the oil and total cylinder firing events.

Additional effects, features and advantages will be apparent in the written description that follows.

BRIEF DESCRIPTION OF THE DRAWINGS

The novel features believed characteristic of the invention are set forth in the appended claims. The invention itself however, and preferred mode of use, further objects and advantages thereof, will best be understood by reference to the following detailed description of an illustrative embodiment when read in conjunction with the accompanying drawings, wherein:

DETAILED DESCRIPTION OF THE INVENTION

Figure 1:
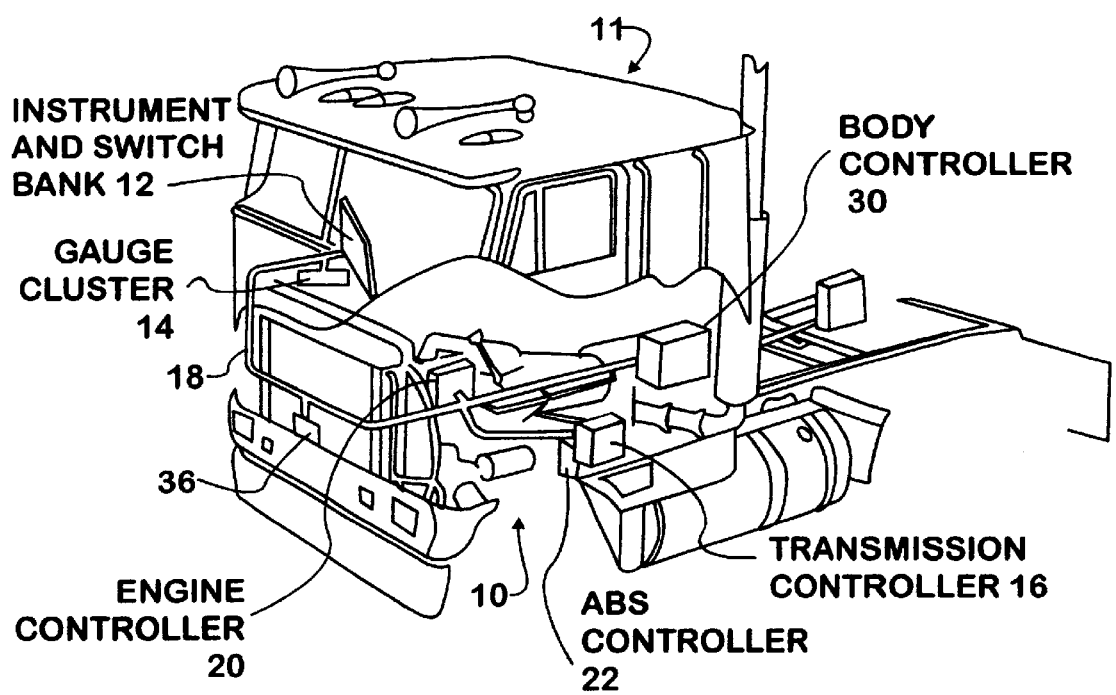
FIG. 1 is a perspective view in partial cutaway of a truck tractor incorporating an engine and a control network.

The present invention extends the model of motor oil deterioration based on available sensor and engine operation telemetry, and provides a computer executed algorithm implementing the model based on the telemetry to generate direct indications of the appropriate time to change motor oil. As already described, in diesel engines soot accumulation, molecular degradation and oxidation of the motor oil are usually the greater factors in engine oil deterioration, although water and coolant infiltration can become major contributors, especially in cases where an engine is damaged.

While brake mean effective pressure (BMEP) provides an excellent indicator of soot blow-by, BMEP is currently difficult, and more importantly, expensive to measure in real time engine applications. BMEP may be estimated as a product of fuel flow and engine RPM. High BMEP is associated with high cylinder pressures produced concurrently with low engine speeds and high fuel flows. This allows use of an alternative formulaic model of for soot blow-by:

$$SOOT = C_0 \int M_f / n \, dt \text{ from } t=0 \text{ to } t=T, \text{ where } M_f \text{ is fuel flow} \quad (3)$$

Here T corresponds to the time in engine operating hours since the last oil change at T=0. The formula may be adjusted for engine wear by changing the scaling factor $C_0$ for total engine hours since an engine build or rebuild. If provided, a look up table can be used based on historical information. Greater blow by is expected from engines as wear increases. The basic engine wear algorithm thus is the sum of SOOT from equation (3) and SHEAR from equation (2).

A complete model must take into account the possibility of loss of oil or intrusion of foreign material into the engine oil. These factors can become important where an engine is damaged or is subjected to unusual operating cycles. For example, if an engine is operated for short cycles, and does not reach or maintain normal operating temperatures, water which has found its way into the oil will not be forced from the oil by evaporation. Where water remains in the engine if provides a solvent for sulphur-hydrogen based compounds produced as a by product of combustion and escaping around the pistons from the combustion chambers. Eventually, engine oil additives used to make water impurities slightly basic will be exhausted and the water in the engine oil will become increasingly acidic with attendant corrosion of the engine components. The model is improved by taking into account the temperature cycling of the engine oil. An approximation of the effect of the engine's temperature cycle is obtained by timing total engine operating time below a threshold temperature.

$$D(t) = d_0 t \quad (4)$$

where t is the cumulative time below the temperature limit since the last oil change.

Engine oil contamination has less predictable effects than soot accumulation, oxidation and shear, and may render the algorithm outlined above valueless. A dielectric sensor within the engine oil may be used to detect the contamination of the oil by water or ethylene glycol. The algorithm may then be extended to cover contamination by impurities. The process accounts for the engine not reaching or maintaining the threshold temperature and indication of a high dielectric level. If a high dielectric coefficient is indicated and engine temperature is higher than the threshold limit, the presence of ethylene glycol is indicated and an alarm should be lit or sounded.

Fuel contamination, and the consequent dilution and loss of viscosity of engine oil can produce problems. In general, this may be caused by fuel injector malfunction and indicated by differential engine speed or cylinder to cylinder power imbalances.

Contemporary diesel engines usually incorporate engine controllers in order to more nearly optimize operation of the engines. Engine controllers are on board digital computers which are connected to a variety of sensors providing data relating to engine operation. Engine controllers may communicate with a more generalized body controller, which in turn may be programmed to provide more sophisticated, higher level treatment of the telemetry produced by the sensors and which may receive additional data inputs not directly available to the engine controller, such as miles traveled since the last oil change, which allow implementation of more sophisticated vehicle operation monitoring programs.

Referring now to the figures and more particularly to FIG. 1, a perspective view of a vehicle 11 and of an electrical control system 10 installed on the vehicle. Vehicle electrical system 10 comprises a twisted pair (either shielded or unshielded) cable operating as a serial data bus 18. One node of bus 18 is a body controller 30, which is a higher level data processing component of electrical control system 10. Body controller 30 manages a number of vocational controllers connected to bus 18 as nodes and disposed on vehicle 11. Preferably, bus 18 and the various nodes attached thereto form a controller area network (CAN).

Active vehicle components are typically controlled by one of a group of autonomous, vocational controllers, which include a gauge cluster 14, an engine controller 20, typically supplied with an engine 19, a transmission controller 16, an auxiliary instrument and switch bank 12, and an antilock brake system (ABS) controller 22, all of which are connected to body controller 30 over a serial data bus 18 and all of which are connected to bus 18 as nodes. The autonomous controllers include local data processing and programming and are typically supplied by the manufacturer of the controlled component. Bus 18 is typically a twisted pair cable usually constructed in accordance with SAE standard J1939 and is externally accessible via a diagnostic port 36. Although the autonomous controllers handle many functions locally and are functionally defined without reference to body controller 30, they nonetheless report data to body controller 30 and can receive operational requests from body controller 30. In this way, diverse operational aspects of vehicle 11 systems may be controlled or monitored by body controller 30. The body controller 30 provides higher level data processing capable of implementing programmed, adaptive routines to improve operation of vehicle 11, including the oil condition monitoring program of the present invention.

Figure 2:
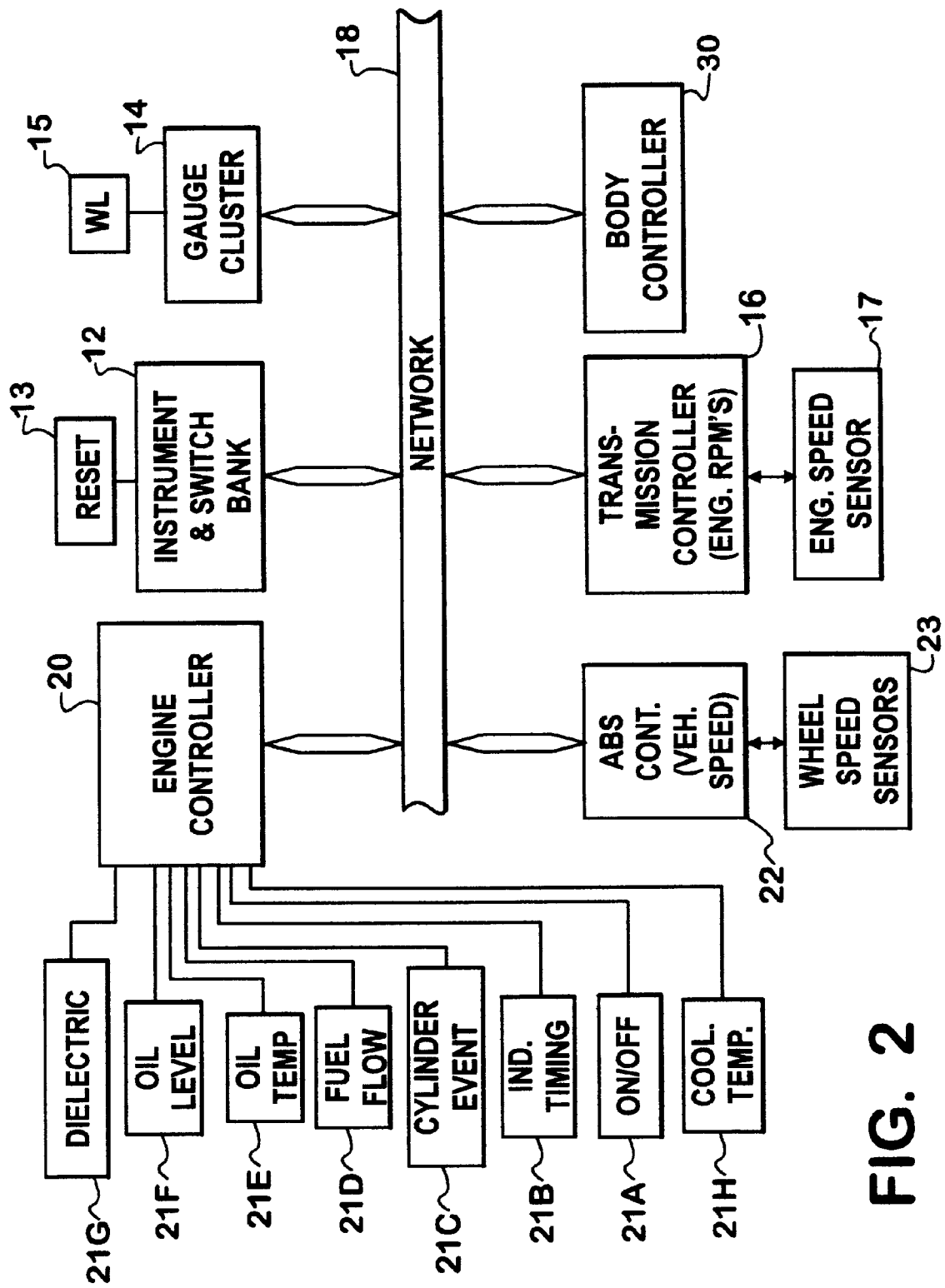
FIG. 2 is a schematic diagram of a vehicle control network.

FIG. 2 illustrates the sources of data relating to vehicle 11 operation, this data can be provided to body controller 30. Engine controller 20 is the source of most of the required data. A series of modules 21A–21G represent sensors connected to engine controller 20 or events under the control of the engine controller. An ON/OFF indication 21A relates to generation of an indication as to whether the engine 19 is running. Timing indicator 21B relates to timing of the injection of fuel into the cylinder in terms of piston position. Cylinder event indicator 21C indicates a burn event in any cylinder. Fuel flow sensor 21D provides a fuel flow measurement. Oil temperature sensor 21E and oil level sensor 21F provide measurement signals for the identified variables, respectively. An engine oil dielectric sensor 21G measures the current dielectric constant of the engine oil. Sensors 21E–G may be combined in one instrument. A coolant temperature sensor 21H provides measurement of the temperature of the coolant.

Engine controller 20 both utilizes the values generated by the indicators and sensors for local purposes and provides for transmission of the data over bus 18 to body controller 30 for use in the oil change algorithm of this invention.

Some data used to practice the invention can come from other sources, including an instrument and switch bank 12, which incorporates a reset button 13 which is used to indicate that an oil change has been performed. Anti-lock brake system controller 22 is connected to a plurality of wheel speed sensors 23, which may be used to generate vehicle speed. The integral of vehicle speed over time is of course distance, which is an input to the full oil change algorithm. Alternatively speed may be measured from the propeller shaft extending from the transmission to a rear differential. A tachometer 17 generates a signal relating to engine RPMs from the engine crankshaft or camshaft. A tachometer 17 is usually realized using a crank or camshaft position indicating device and comparing that output against time. The raw tachometer signal then can be used to determine piston position in the cylinders and "timing" fuel injection. A gauge cluster 14 is connected to warning lights 15, which may be illuminated on demand from body controller 30. Body controller 30 tracks total miles traveled and times engine operation. Controller 30 provides a storage location for the program implementing oil condition monitoring and its execution.

Figure 3A:
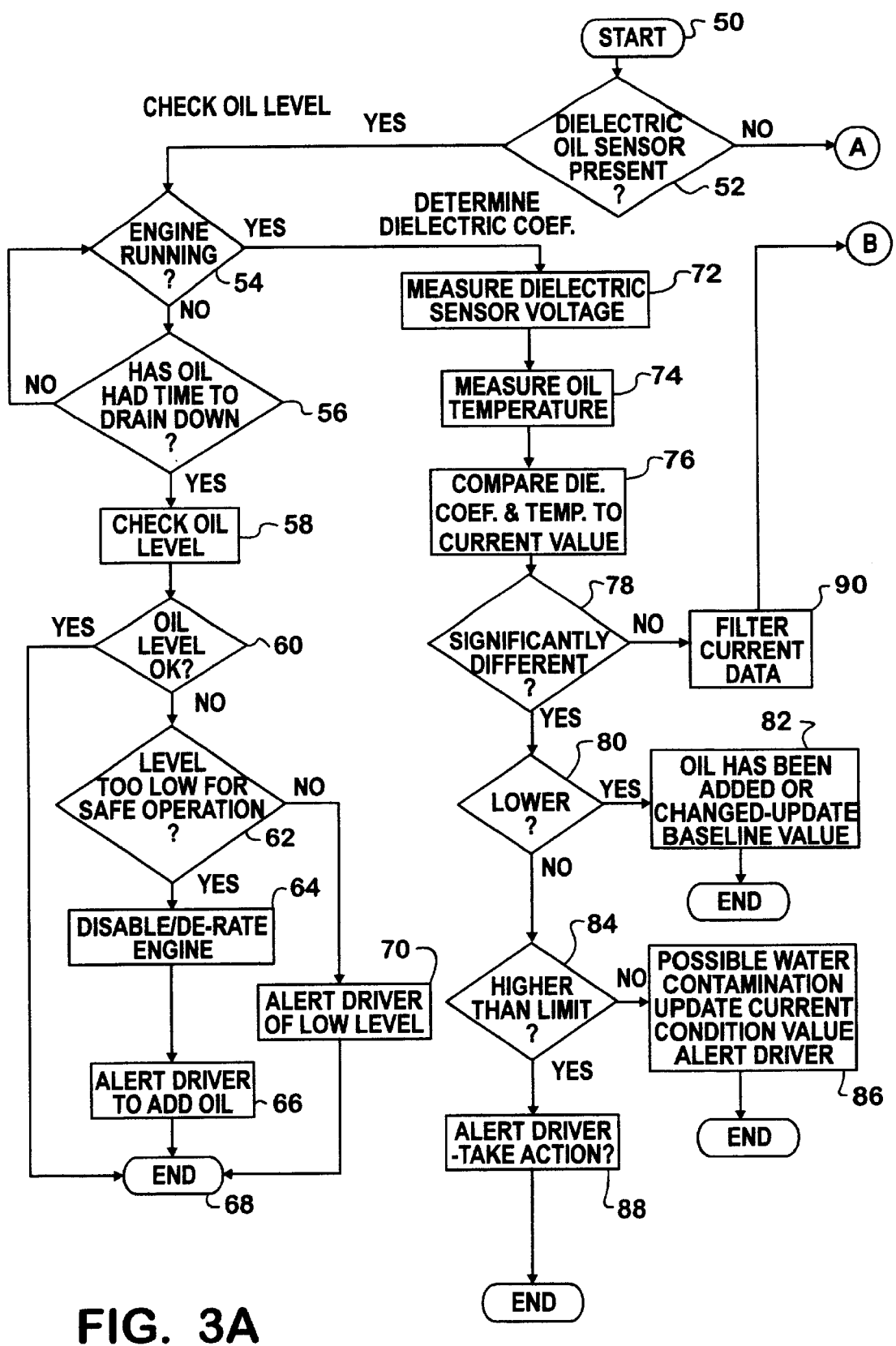
FIG. 3 is an overall flow chart illustrating the method of the present invention for determining timing of engine oil changes.
Figure 3B:
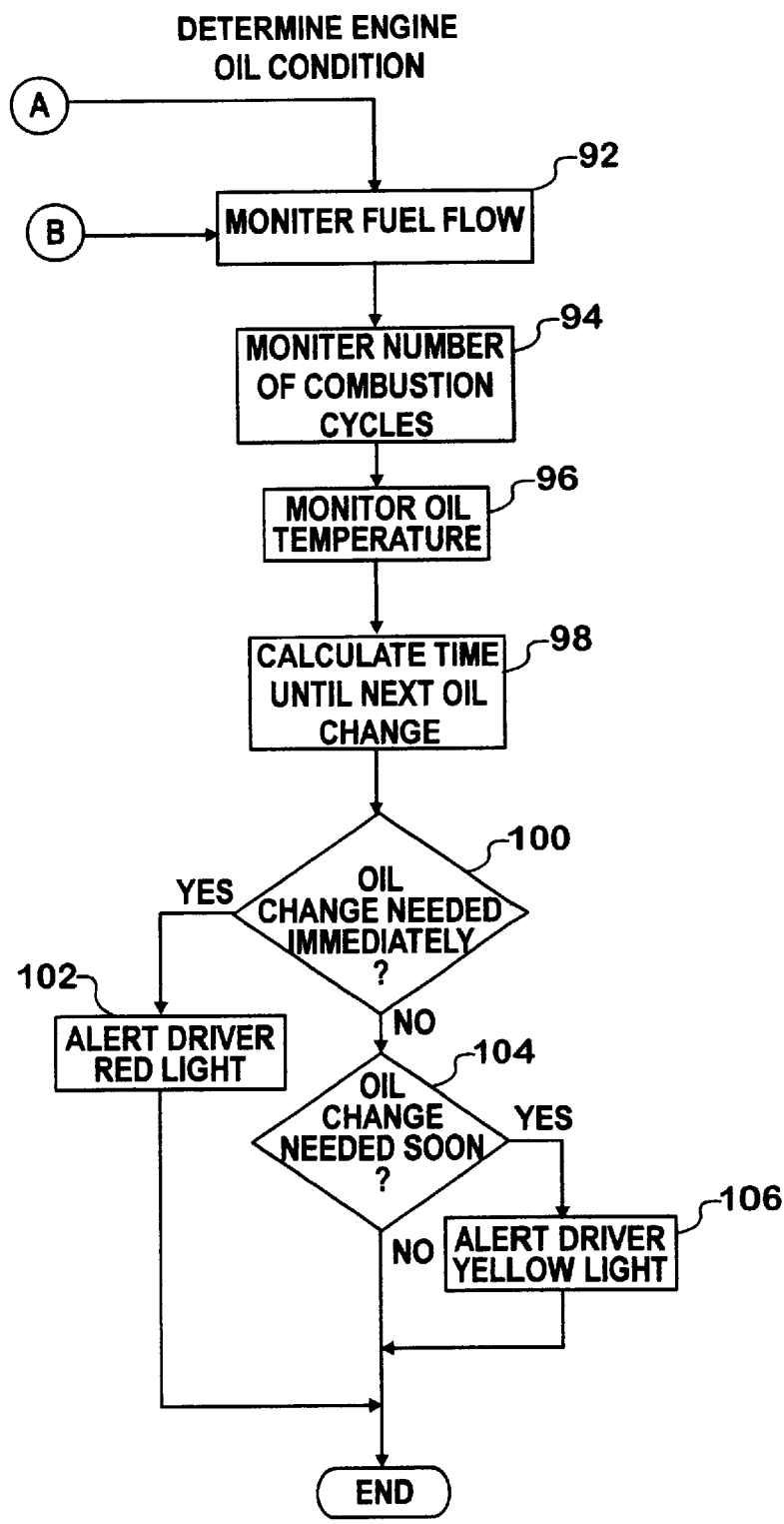

FIG. 3 is an overall flow chart of the algorithm implemented by in the preferred embodiment of the invention which resides and is executed in the body controller using data supplied by other autonomous controllers. Execution of the algorithm begins upon an ignition switch being moved from an off to an on position, even without starting engine 19. Upon start 50 of the routine, determination of the presence of a dielectric sensor is immediately initiated at step 52. The presence of a dielectric sensor in contact with the engine oil has substantive consequences for the path execution of the algorithm takes.

If a dielectric oil sensor is present, an engine oil level check may be performed. This is done only if the engine is not running, and has not run for a period long enough to allow motor oil to collect in the vehicle sump. Oil level checking is done against two minimums, a first minimum sufficient to allow normal vehicle operation and a second minimum which allows operation but results in a warning to the driver. Failure to meet both minimums results in the derating or disabling of the engine and causes a caution to be issued to the operator to add oil. Accordingly, along the YES branch of the algorithm from step 52, indicating the presence of an oil dielectric constant sensor, step 54 provides for determining if the engine is running. If the engine is not running (the NO branch) oil level may be checked. The elapsed time since engine 19 has been shut down is monitored in a loop controlled by decision block 56. If sufficient time has elapsed for an oil level check to be performed the YES branch is taken from step 56, if however, the engine is started before the oil can drain the algorithm exits the loop from step 54. Once the YES branch is taken from step 56 the engine oil level is checked (step 58). If the oil level is above an acceptable minimum for normal operation the routine exits along the YES branch from step 60. If the oil level does not meet the minimum for normal operation, the level is compared to another, lower minimum level. If this second, lower minimum is not met (the YES branch from step 62), the engine may be disabled or derated (step 64) and the driver alerted to add oil (step 66). The routine is then exited. If the oil level is not too low for safe operation the NO branch from step 62 advances execution to step 70, where the driver is alerted to the low oil level condition.

Once the engine is started, monitoring of the engine oil dielectric constant may begin, provided a dielectric sensor is present. Returning to step 54 and following the YES branch, the algorithm moves to a series of steps, represented by execution step 72, used to determine the dielectric constant of the oil. The use of the dielectric constant is elaborated upon in greater detail with reference to FIG. 6. Oil temperature is measured at step 74. Steps 76 and 78 provide for comparing the measurements with reference values for departure from expected values. If the measurements depart substantially from the reference values it is taken as an indication either that something is potentially wrong or that there as been a change in operating condition of the truck.

Departures from expected values can of course occur in two directions, below or above expected values. The YES branch from step 78 is followed upon departure of the measurements significantly from expected values. A filter 80 for lower than expected values follows detection of an out of bound condition at step 78. It should be noted that the out of operational bound conditions used in steps 80 and 84 are not the same as the limit values used as triggers indicating a significant change in step 78. In other words, a short term substantial change in the dielectric coefficient, even if not outside of operating limits, is in itself a possible indication of trouble, depending on the direction of the change. If dielectric constant is lower than expected, it is taken as an indication that motor oil has been added since the last measurement or that the oil has been changed. The YES branch is taken from filter step 80 to step 82 to update the baseline value for the dielectric, that is, changing the value used for the comparison in step 78. If the values are not lower than expected, processing continues from step 80 to step 84, where out of bounds operation to the high side are checked for. Here a NO result is taken as an indication of possible water contamination of the oil (step 86). The condition variable is updated and the driver/operator alerted as to the condition. If the result in step 84 is a measured value above the operating limit the driver is alerted to the fact and advised to take immediate action.

A truck which does not have a dielectric sensor implements an abbreviated algorithm. This portion of the algorithm implements the basic soot and shear estimation model and is also implemented by trucks having dielectric sensors after completion of the dielectric constant and temperature measurements and the updating (filtering) of constants (step 90) used for comparison purposes at steps 76 and 78. By filtering, it is meant that a time weighted average of data points is used, with more recent measurements weighted more heavily than earlier measurements.

The model is described in greater detail below with reference to the detailed flow charts. The overall process of soot, oxidation and shear modeling begins with monitoring fuel flow (step 92), counting the number of combustion cycles (step 94), monitoring the oil temperature (step 96) and updating the estimated distance until the next oil change (step 98). Should conditions indicate the need for an immediate oil change (step 100), YES branch is followed and the driver is alerted (step 102). Along the NO branch from step 100 it is determined if the time for an oil change is imminent (step 104), and if so the driver is alerted with a yellow colored warning light (step 106 along the YES branch from step 104).

Figure 4:
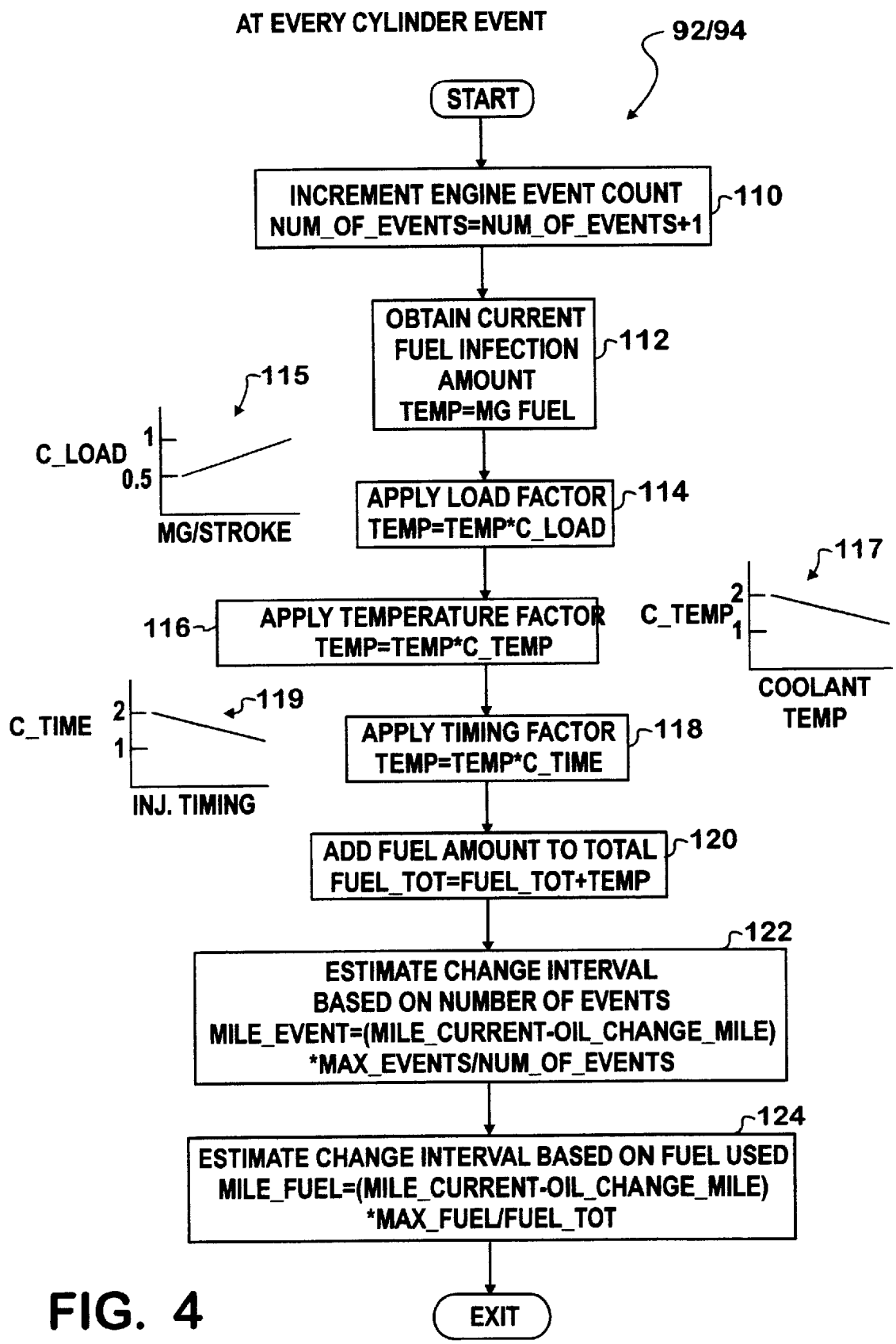
FIG. 4 is a flow chart illustrating a fuel flow portion of the algorithm.

Each firing of a cylinder represents a soot contributing event. FIG. 4 expands upon steps 92 and 94 of the flow chart of FIG. 3, illustrating updating of the soot accumulation estimation for the motor oil. Soot addition is estimated as a function of fuel flow, load, coolant temperature and an injection timing factor. At each cylinder event a count of cylinder events (Num_of_events) is incremented by 1 (step 110). Then the current fuel flow is used to obtain an injection amount in milligrams (step 112). The injection amount (fuel_amount) is stored as a temporary variable (Temp). Increasing engine load is indicated by increasing fuel flow without a contemporaneous increase in engine RPM's. The load coefficient C_load is illustrated in graph 115, which represents an updatable look up table, as an increasing function of milligrams of fuel flow per piston stroke. At step 114 the temporary variable is updated by multiplying the current measured injected amount of fuel with the load coefficient producing an updated temp variable. Soot blow by is reduced by thermal expansion of a piston in a cylinder, and accordingly soot accumulation in engine oil is a falling function of engine temperature as indicated in graph 117, which represents a look up table. At step 116 the Temp variable is updated by multiplying Temp from step 114 with the temperature coefficient C_temp obtained from a look up table represented by graph 117. Soot transfer from cylinder to lubricating oil is a function of piston position. A look up table represented by graph 119 indicates the likely amount of soot transferred in a stroke based on how much of the interior cylinder wall is exposed when fuel is injected. This occurs because the oil film on the cylinder wall absorbs oil. The closer to top dead center that injection is initiated the less of the wall is exposed and accordingly graph 119 is drawn indicating that timing transfer coefficient C_time decreases as the injection timing approaches top dead center (TDC). Temp from step 116 is multiplied by C_time to update the Temp variable.

Finally, Temp is added to total fuel (Fuel_tot) at step 120 to generate an updated value for Fuel_tot. In effect, FIG. 4 illustrates an implementation of the equation:

$$\text{Fuel\_tot}_n = \text{Fuel\_tot}_{n-1} + C\_time * C\_temp * C\_load * fuel\_amount \quad (5)$$

Two provisional estimates of the distance to the next oil change, based on events and fuel flow, are then made. At step 122 the count of the number of events (Num_of_events) is used as a variable in equation (6):

$$\text{Mile\_event} = (\text{Mile\_current} - \text{Oil\_change\_mile}) * (\text{Max\_events}/\text{Num\_of\_events}) \quad (6)$$

And at step 124 Fuel_tot is used to generate an estimate of "Mile_fuel" in equation (7)

$$\text{Mile\_fuel} = (\text{Mile\_current} - \text{Oil\_change\_mile}) * \text{Max\_fuel}/\text{Fuel\_tot}. \quad (7)$$

Figure 5:
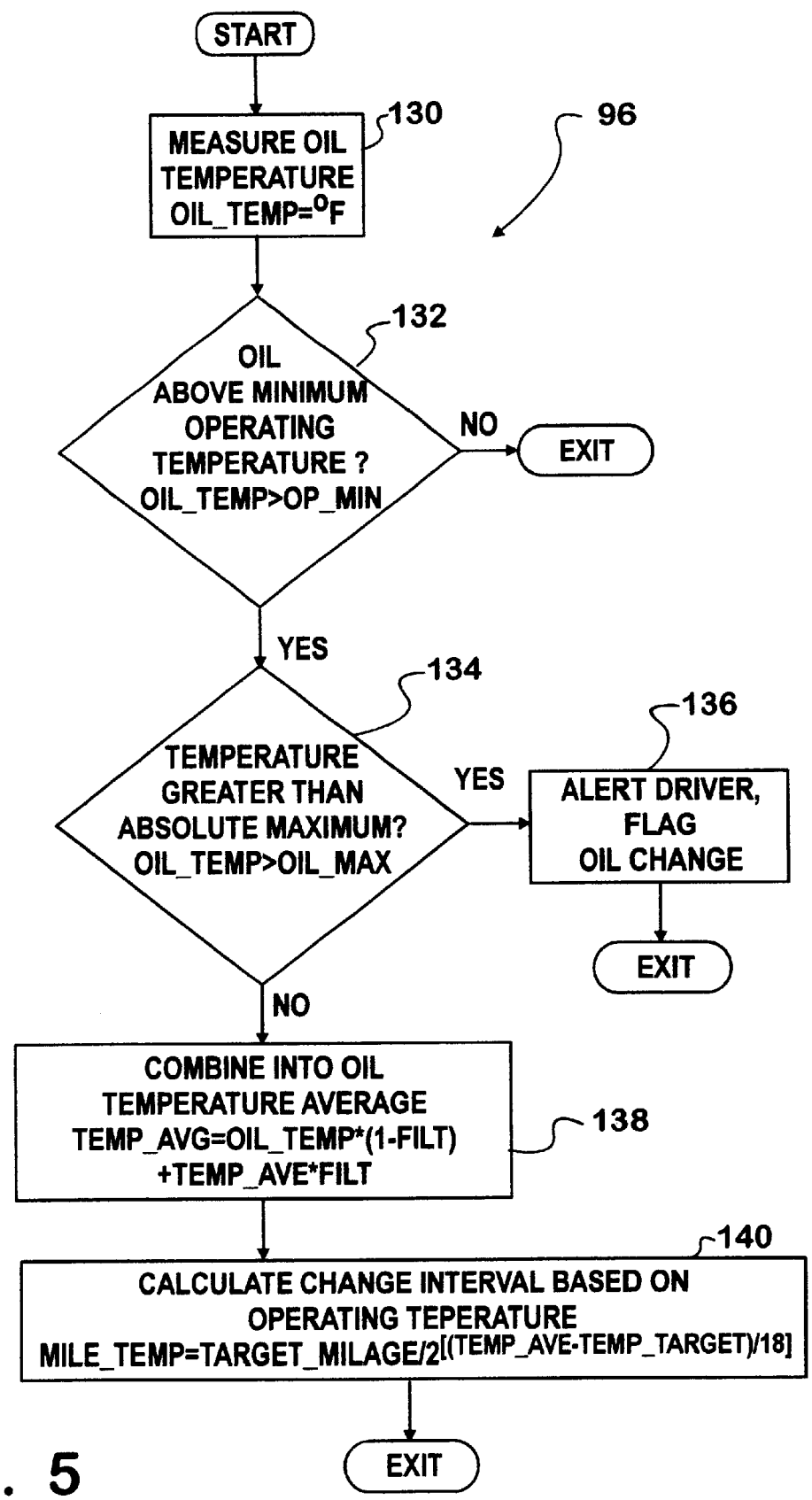
FIG. 5 is a flow chart illustrating the oil temperature portion of the algorithm.

FIG. 5 illustrates measurement of oil temperature and utilization of the oil temperature data, expanding upon step 96 of FIG. 3. Excessive oil temperature contributes to oxidation of the oil. Step 130 indicates the reading of an oil temperature measurement. At step 132 the measured temperature of the oil is compared to an operating minimum. If the oil temperature does not yet exceed the minimum the routine is exited. Temperature measurements of the lubricating oil below a minimum threshold are disregarded to avoid skewing the calculated average toward a lower temperature. If the temperature exceeds the minimum, the YES branch is followed to step 134 where the measured temperature is compared to an maximum. If the temperature exceeds the maximum, the YES branch is followed to step 136, providing for alerting the driver and flagging an oil change. The NO branch from decision step 134 is followed to step 138, which provides for updating a variable tracking the operating history of the oil in the form of an oil temperature average.

$$\text{Temp\_ave} = \text{Oil\_temp} * (1 - \text{Filt}) + \text{Temp\_ave} * \text{Filt}, \quad (8)$$

Where Filt is a Filter constant with a value between 0 and 1 that determines how frequently the average is updated. A small Filt value means it takes a long time for the average to change and large value for Filt means that the average changes quickly.

Next, at step 140, a change interval is calculated based on oil operating temperature.

$$\text{Mile\_temp} = \text{Target\_mileage}/2^{[(\text{Temp\_ave} - \text{Temp\_target})/18]}. \quad (9)$$

Equation (9) is applicable where the temperature measurement is in degrees Fahrenheit or Rankine. For temperature measurements in Kelvins or degrees Celsius substitute 10 for 18 in the equation.

Figure 6:
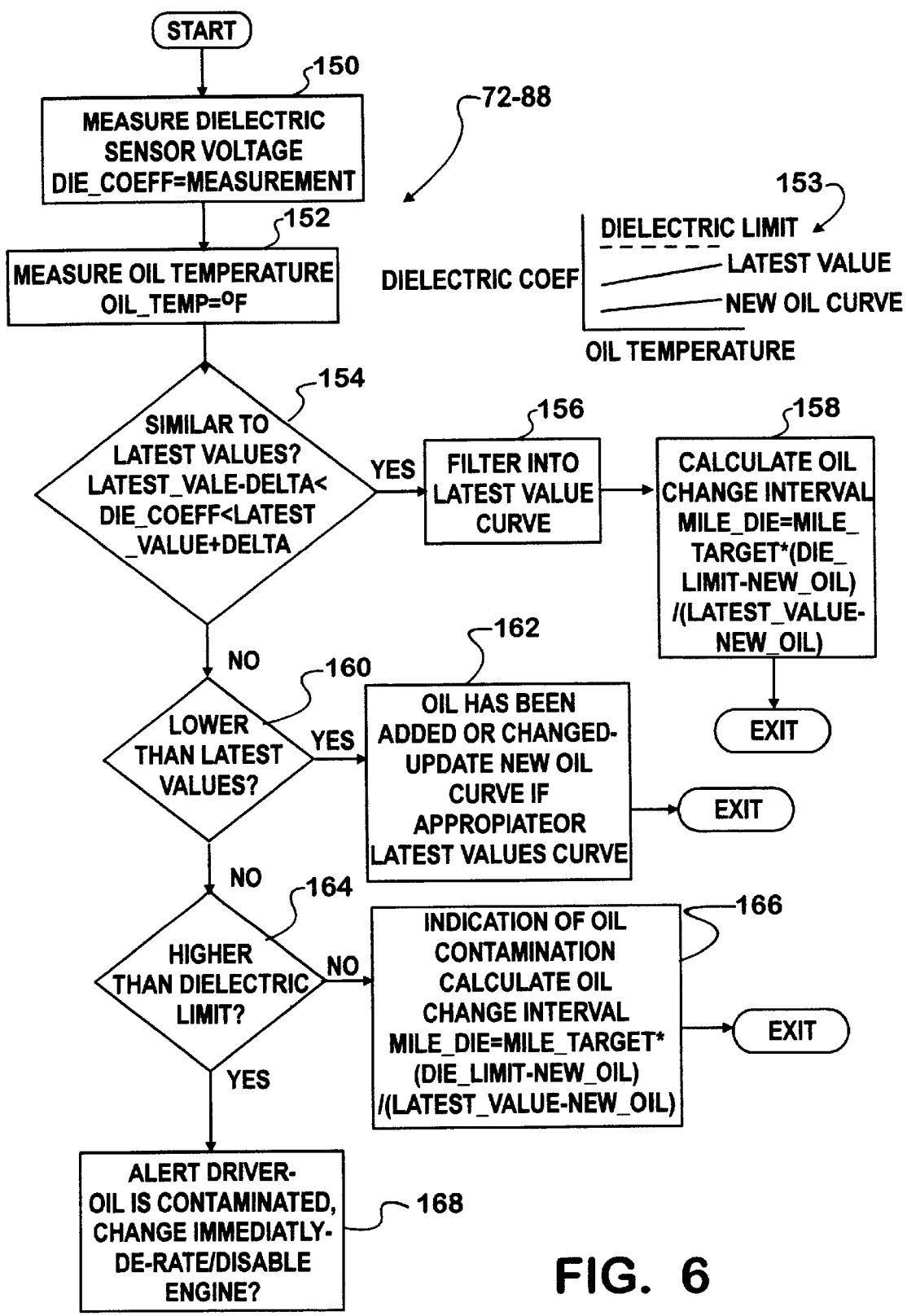
FIG. 6 is a flow chart illustrating oil dielectric measurement.

Referring now to FIG. 6, steps 72 to 88 of FIG. 3, which relate analysis of oil dielectric constants on a vehicle equipped with the appropriate sensor, are expanded upon. Beginning at step 150, the voltage across the dielectric sensor is measured and equated to the dielectric coefficient. Next, at step 152, the temperature of the oil is taken. The dielectric "constant" or coefficient of the oil is a function of oil temperature. The oil's dielectric coefficient also tends to increase slowly over time. Using the measured temperature, a look up table 153 may be referred to in order to obtain a predicted value for the dielectric coefficient at the present measured temperature. Essentially, the dielectric coefficient should be close to recently obtained values, averages for which provide the values in look up table 153. Comparative curves for new oil and hypothetical recent values are illustrated exemplifying how the dielectric constant moves higher as the engine oil ages.

Oil, the dielectric coefficient for which changes upwardly suddenly has likely been contaminated. A sudden downward shift in the constant usually indicates that fresh oil has been added to an engine or that an oil change has been made. Step 154 provides for determining if such a sudden change in the dielectric coefficient has occurred by checking to see if the coefficient is between upper and lower bounds set based on the recent values for the constant. If the values remain within bounds the just obtained value is filtered into the values used for determining the most recent curve for look up table 153 (step 156) and a new oil change interval calculated (step 158).

$$\text{Mile\_die} = \text{Mile\_Target} * (\text{die\_limit} - \text{New\_oil}) / (\text{Latest\_value} - \text{New\_oil}) \quad (10)$$

If the newly obtained value for Die_coeff is not within bounds the NO branch is followed to step 160, which checks to see if the variation was below the limit. If YES, then oil has been added or the oil has been changed. Step 162 is executed to generate a new curve for look up table 153. Moving along the NO path from step 160 is indication that the oil's dielectric coefficient is outside of the bounds expected. At step 164 it is determined whether the oil's dielectric coefficient is also higher than the absolute dielectric limit. If YES, step 168 provides for alerting the driver and possibly derating or disabling the engine to avoid damage to the engine. If the oil's dielectric coefficient is not above the maximum limit the variation is still an indication of possible contamination and a change interval is recalculated as per equation (10) at step 166.

Figure 7:
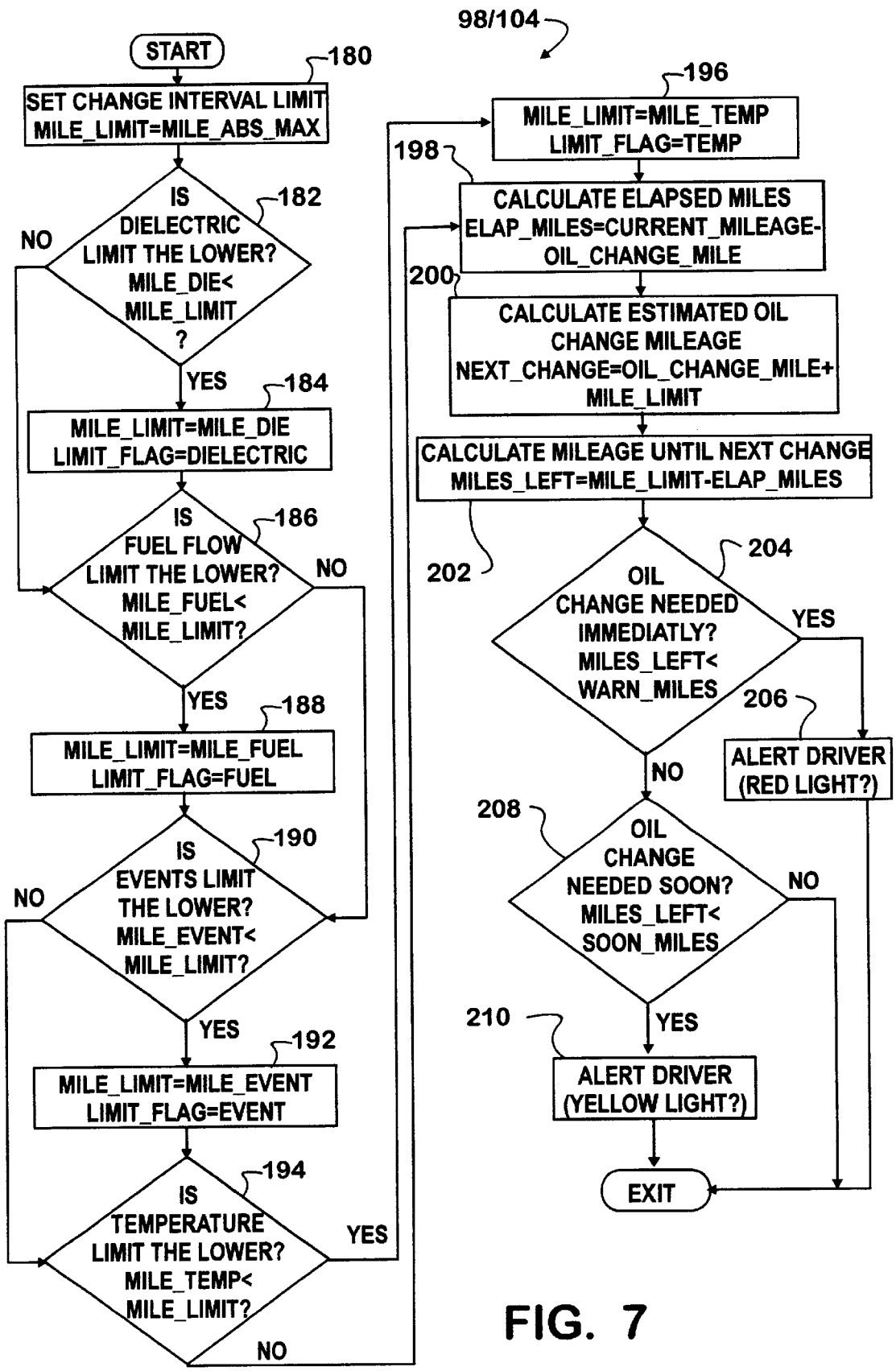
FIG. 7 is flow chart of the algorithm combining the oil change factors.

FIG. 7 is an expansion on steps 98–104, involving determination of the change interval for motor oil. The initial portion of the algorithm here involves a series of comparisons performed on the estimates for change internals already generated to determine the primary contributing factor to the deterioration of the motor oil. The system provides for initializing a variable Mile_limit to the absolute maximum permitted value, Mile_abs_max at step 180. While the variable names used here include the term "mile" the actual variable values may represent kilometers.

The comparison operations are as follows. At step 182, it is determined if the value Mile_die, representing a change interval estimate from either step 158 or step 166 relating to the dielectric constant for the oil, is less than Mile_limit. If YES, then step 184 provides for resetting Mile_limit to Mile_die and for setting a variable Limit flag equal to indicate that the dielectric constant controlled. Following step 184 or the NO branch from step 182, step 186 is executed where the value Mile_fuel, generated at step 124 and representing a change interval estimate based on fuel consumption and other factors, is compared to Mile_limit. If Mile_fuel is lower than Mile_limit, the YES branch directs execution to step 188 where Mile_limit is reset to the Mile_fuel change interval estimate and a flag is set to indicate the source of the Mile_limit value. Along the NO branch from step 186 the reset step 188 is skipped. Following step 188 or along the NO branch from step 186 the value for Mile_event is compared to Mile_limit. Mile_event is the value generated at step 122 relating to a change interval accounting for the total number of cylinder firings that have occurred. Again along a YES branch from the comparison step 190, a variable reset is performed where Mile_limit is reset to equal Mile_event and a Limit_flag is set indicating that the source of Mile_limit is the events estimate. The NO branch provides for skipping step 192, whereupon step 194 is executed, providing for comparison of the mileage change interval estimate based engine oil temperature cycling Mile_temp to the current value of Mile_limit. If YES, step 196 provides for resetting Mile_limit to Mile_temp and setting a flag to indicate that temperature measurements are the source of the current Mile_limit value. Following step 196 or the NO branch from decision step 194 execution advances to a series of steps, beginning at step 198, relating to actual calculation of the distance allowed until the next oil change.

A series of steps is now executed which relate to calculation of the distance left until a change is required and the mileage reading for that change. At step 198 the total elapsed miles (Elap_miles) since the last oil change is calculated. Next, at step 200 the mileage at which the next change should be done (Next_change) is calculated by adding Mile_limit to Oil change mile. The distance left until the next change (Miles_left) is then calculated at step 202 by subtracting Elap_miles from Mile_limit.

The value Mile_left is then used as an input to a series of steps used to determine if the operator should be advised of engine oil condition and the imminent or immediate requirement of an oil change. These steps involve operations comparing Miles_left to two preset values "Warn_miles", used to detect a need for an immediate oil change, and "Soon_miles" used to determine if an oil change will be needed soon (steps 204 and 208, respectively). Depending upon the results of the comparisons, steps 206 or step 210 may be executed to alert a driver of the need to immediately change the oil or that an oil change requirement will come soon (the YES branch from steps 204 or 208). The alternative of no warning is possible by the NO branches from both steps 204 and 208. The vehicle operator can initiate a query to the body controller 30 to find out the estimate of miles left until an oil change is required and what the limiting factor (e.g. shear, temperature, soot) is forcing the result. The operator can then schedule maintenance and adjust vehicle scheduling to match the estimate.

Figure 8:
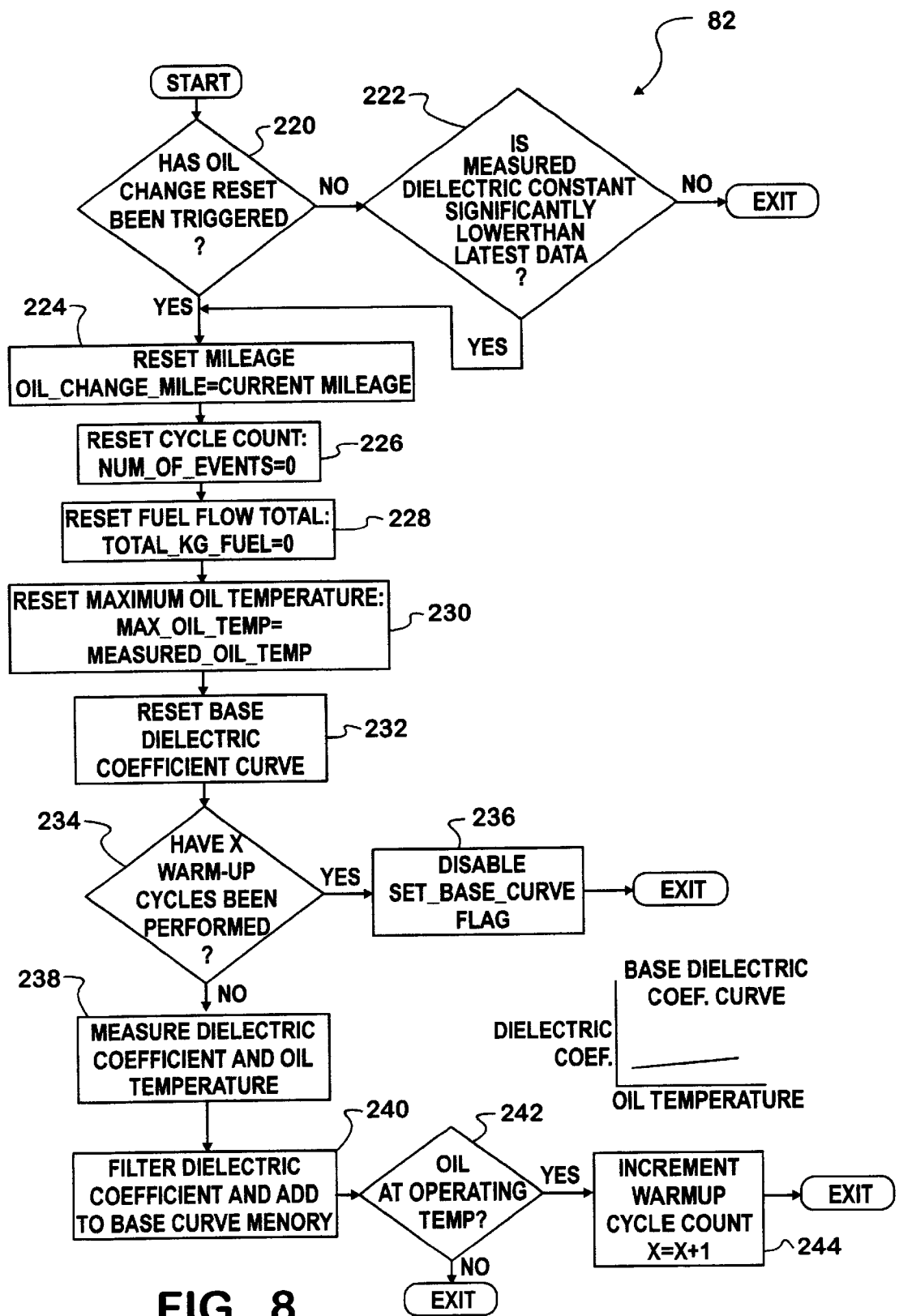
FIG. 8 is a flow chart of a reset algorithm executed after an oil change.

The oil change recommendation algorithm of the present invention must provide for qualitative improvements to engine oil provided either by the addition of oil to the engine or a change of the oil. FIG. 8 corresponds to box 82 of FIG. 3. The process begins at step 220, which determines if an oil change reset has been manually triggered. If YES, processing advances to a series of variable reset steps. If NO, processing moves to a second comparison step 222, which is used to determine if the measured dielectric has substantially changed from a filtered set of recently sampled values. If YES, program execution still proceeds along the set of variable reset steps. If the NO branch from step 222 is taken, the routine is exited.

A total of five variables are reset if an oil change or addition is indicated. Steps 224, 226, 228, 230, and 232 provide for reset for the variables: Oil_change_mile, which is set to the current odometer reading; Num_of_events, the count of cylinder firings, which is set to 0; fuel flow Total_kg_fuel, which is set to 0; Max_oil_temp which is set to the current measured oil temperature; and the base dielectric coefficient curve (look up table).

Resetting the dielectric coefficient curve requires a plurality of measurements. The dielectric constant measurement which is provided immediately after an oil change or an addition of oil will be inaccurate due to the presence of older, fouled oil on the sensor. Until the old oil has been flushed away after a change, or new oil added to old oil has been thoroughly mixed into the old oil, readings from a dielectric sensor will be subject to change. Until a minimum number of engine warm up cycles has occurred, the process remains in the measurement cycle. Reinitialization must also occur after an oil change since different oil formulations have different dielectric characteristics. Some oils exhibit an increasing dielectric coefficient with temperature and some exhibit a decreasing coefficient with temperature, and they all change at differing rates. Following the NO branch from step 234, dielectric measurements and oil temperature measurements are made (step 238) and the dielectric sample is filtered and added to the base curve (step 240). Once the engine oil reached the rated operating temperature (determined at comparison step 242) processing advances to increment the warm-up cycle count (step 244). Once a minimum number X warm-up cycles have been performed, sufficient to extend beyond the minimum mixing period for the oil, the collection of data is deemed complete (step 234) and the set_base_curve_flag is disabled (step 236), allowing look up table 153 to be used.

Table of Variable Definitions

In equation (1):
"$C_o$" is a proportionality constant;
"BMEP" is brake mean effective pressure;
"dn" is change in n;
"n" is engine revolutions; and
"SOOT" is milligrams of contaminants including unburned and partially burned hydrocarbon fuels.

In equation (2):
"SHEAR" is an index;
"$K_o$" is a proportionality constant;
"dn" is change in n; and
"n" is engine revolutions.

In equation (3):
"n" is engine revolutions;
"$M_f$" is fuel flow; and
"dt" is change in time.

In equation (4):
"$d_0$" is a proportionality constant; and
"t" is time.

In equations (5–7) and steps 110 to 124 of FIG. 4:
"Num_of_events" is a program counter based on cylinder fuel injection events;
"Temp" is a temporary variable accumulating soot passed from cylinder to oil per cylinder event;
"fuel_amount" is the amount of fuel injected per cylinder event by weight in mg;
"C_load" is a load coefficient related to milligrams of fuel injected per stroke provided by table 115;
"C_temp" is a leakage coefficient related to coolant temperature provided by table 117;
"C_time" is a timing coefficient provided by a look up table 119 related to the difference time between fuel injection and the piston for the cylinder in question being at top dead center;
"Fuel_tot" is the accumulated material passed to engine lubricating oil, i.e. the proxy for SOOT implemented by the model of the invention;
"Mile_fuel" is the estimated odometer reading when accumulated material in the lubricating oil will require an oil change. The units can be miles or kilometers;
"Mile_current" is the current odometer reading in miles or kilometers;
"Oil_change_mile" was the odometer reading at the time of the last oil change;
"Max_fuel" is the limit of accumulated material allowed in the engine oil;
"Mile_event" is the estimated odometer reading in miles or kilometers when the number of cylinder events will reach the maximum allowed without an oil change; and
"Max_events" is the maximum number of allowed cylinder events.

In equations 8 and 9 and steps 130 to 140 of FIG. 5:
"Oil_temp" is measured oil temperature in degrees Fahrenheit or Celsius;
"Filt" is a filter constant between 0 and 1 that determines how frequently oil temperature averages are updated;
"Temp_ave" is averaged oil temperature;
"Op_min" is a minimum oil temperature threshold;
"Op_max" is an upper limit oil operating temperature;
"Mile_temp" or mile temperature is the estimated oil change interval based on temperature history of the oil; and
"Target_mileage" is a change interval based on nominal temperature operating history.

In equation 10 and steps 150 to 166 of FIG. 6:
"Die_Coeff" is dielectric coefficient of the oil;
"Oil_temp" is oil temperature;
"delta" is the maximum change is dielectric value allowed since the last measurement;
"Mile_die" is the estimated oil change interval in miles or kilometers based on the oil's measured dielectric value;
"Mile_Target" is a target mileage interval between changes of oil necessitated by the dielectric coefficient of the oil;
"die_limit" is the maximum allowed dielectric coefficient for the oil;
"New_oil" is the new oil dielectric coefficient; and
"Latest_value" is the most recent measurement of dielectric coefficient.

New variable introduced in steps 180 to 210 of FIG. 7:
"Mile_abs_max" is the absolute maximum allowed change interval. Initially
"Mile_limit" is set equal to this value;
"Elap_miles" is elapsed miles, the difference between the current odometer reading and the odometer reading at the time the oil was last changed;
"Warn_miles" and "Soon_miles" are mileage values used in comparison steps.

The present invention provides for indicating timing of oil changes based upon measurement of engine operating variables. Most of the measurements are derived from existing sensors, with the possible exception of the addition of a dielectric sensor to the engine oil. Such a dielectric sensor can be substituted for existing level sensors. Obviously, low engine oil lubricating level from a dielectric sensor can also be a source of a warning signal to add oil.

While the invention is shown in only one of its forms, it is not thus limited but is susceptible to various changes and modifications without departing from the spirit and scope of the invention.

What is claimed is:

1. An control mechanism for an internal combustion engine providing indication of a need to change lubricating oil in the internal combustion engine, the control mechanism comprising:

a plurality of sensors coupled to the internal combustion engine providing engine data relating to brake mean effective pressure, lubricating oil temperature, engine coolant temperature, dielectric coefficient of the lubricating oil, lubricating oil level, fuel flow, engine rotational speed and firing timing;

a computer connected to receive the engine data and including data storage space to retain accumulated and filtered measurements based on the engine data;

a program stored on the computer embodying a model of lubricating oil condition based on the engine data and the accumulated and filtered measurements based on the engine data; and said program including steps for:
 determining engine load from fuel flow and engine speed;
 developing adjustment coefficients based on engine load, temperature and piston timing;
 estimating soot being added to the lubricating oil from each cylinder event by multiplying a fuel injection quantity for the cylinder event by the adjustment coefficients;
 accumulating an estimate of total soot in the lubricating oil by summing the estimated soot figures for each cylinder event; and
 relating the estimate of total soot to a soot oil change interval.

2. The control mechanism of claim 1, wherein the program further comprises modules providing:
 a history of the lubricating oil temperature measurements generating therefrom an estimate of oxidation of the lubricating oil obtained from temperature cycles of the lubricating oil; and
 relating the history of oil temperature measurements as a proxy for oxidation of the oil to an oxidation oil change interval.

3. The control mechanism of claim 2, wherein the program further comprises modules providing:
 a chart of expected lubricating oil dielectric coefficients against lubricating oil temperature.

4. The control mechanism of claim 3, wherein the program further comprises modules:
 responsive to operator request to provide the current mileage until an oil change is required and what limiting factor determines the mileage estimate.

* * * * *